US008394762B2

United States Patent
Wynne et al.

(10) Patent No.: US 8,394,762 B2
(45) Date of Patent: Mar. 12, 2013

(54) SELF-DECONTAMINATING COATINGS CONTAINING ANTIMICROBIAL PEPTIDES

(75) Inventors: James H Wynne, Alexandria, VA (US); Preston A Fulmer, Richmond, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/097,175

(22) Filed: Apr. 29, 2011

(65) Prior Publication Data

US 2011/0269669 A1 Nov. 3, 2011

Related U.S. Application Data

(60) Provisional application No. 61/329,522, filed on Apr. 29, 2010.

(51) Int. Cl.
*A61P 31/04* (2006.01)

(52) U.S. Cl. .......... 514/2.4; 514/21.4; 514/23; 424/405; 424/409; 424/486

(58) Field of Classification Search .................. None
See application file for complete search history.

(56) References Cited

U.S. PATENT DOCUMENTS

2003/0194445 A1* 10/2003 Kuhner et al. ............... 424/622

OTHER PUBLICATIONS

Fulmer P.A. et al; "Development of antimicrobial peptides (AMPs) for use in self-decontaminating coatings." Appl. Mat. & interf. (2010) 2(4) p. 1266-1270. Published online Mar. 22, 2010.*
Iijima N. et al; "Purification and characterization of three isoforms of chrysophsin, a novel antimicrobial peptide in the gills of the red sea bream, Chrysophrys Major." Eur. J. Biochem. (2003) 270 p. 675-686.*
Brock, T. D. et al, Biology of Microorganisms, Prentice-Hall, NJ, (1984) p. 228.*
Iijima, N. et al; "Purification and characterization of three isoforms of chrysophsin, a novel antimicrobial peptide in the gills of the red sea bream, Chysophrys major." Eur. J. Biochem. (2003) 270 p. 675-686.*
Darouiche, Clinical Infectious Diseases 2003, 36, 1284-1289.
Decraene et al., Applied and Environmental Microbiology 2006, 72, 4436-4439.
Hilpert et al., Chemistry & Biology 2009, 16, 58-69.
Iijima et al., Eur J Biochem 2003, 270, 675-86.
Mason et al., Biochemistry 2007, 46, 15175-87.
Punyani et al., Journal of Applied Polymer Science 2006, 102, 1038-1044.
Rhoades et al., "Oligopeptides as antimicrobial agents in aqueous polymer systems." Abstracts of Papers of the American Chemical Society 2005, 230, U4039-U4040.
Statz et al., Biofouling 2008, 24, 439-448.
Wicks et al., "Investigation of Antimicrobial Peptide Sales: Efficacy and Solubility in Surfactant Solutions for Latex Systems" Combinatorial Methods and Informatics in Materials Science 2006, 894, 139-146.

* cited by examiner

*Primary Examiner* — Cecilia J Tsang
*Assistant Examiner* — Fred Reynolds
(74) *Attorney, Agent, or Firm* — Amy L. Ressing; Joseph T. Grunkemeyer

(57) ABSTRACT

Disclosed herein is a composition having: a polymeric material and an antimicrobial peptide derived from *Chrysophrys major*. Also disclosed herein is a method of: combining the polymeric material and antimicrobial peptide to form a coating material, and applying the coating material to a surface.

6 Claims, 2 Drawing Sheets

SELF-DECONTAMINATING COATINGS CONTAINING ANTIMICROBIAL PEPTIDES

This application claims the benefit of U.S. Provisional Application No. 61/329,522, filed on Apr. 29, 2010. The provisional application and all other publications and patent documents referred to throughout this nonprovisional application are incorporated herein by reference.

TECHNICAL FIELD

The present disclosure is generally related to self-decontaminating coatings.

DESCRIPTION OF RELATED ART

With the increase of antibiotic resistant microbes, interest in the production of self-decontaminating surfaces has become an area of research that has seen a surge of interest in recent years (Decraene et al., *Applied and Environmental Microbiology* 2006, 72, 4436-4439; Punyani et al., *Journal of Applied Polymer Science* 2006, 102, 1038-1044). Such surfaces, when incorporated into commercial products such as children's toys (Nzeako et al., *British Journal of Biomedical Science* 2006, 63, 55-58), medical devices (Babu et al., *Biomaterials* 2006, 27, 4304-4314; Eby et al., *ACS Applied Materials & Interfaces* 2009, 1, 1553-1560; Eludes et al, *Biomaterials* 2007, 28, 2869-2875) and hospital surfaces (Decraene et al., *Infection Control and Hospital Epidemiology* 2008, 29, 1181-1184; Decraene et al., *Current Microbiology* 2008, 57, 269-273), could reduce the number of infections caused by pathogenic bacteria. A number of active components for self-decontaminating surfaces have been investigated, including common antibiotics (Darouiche, *Clinical Infectious Diseases* 2003, 36, 1284-1289; Gollwitzer et al., *Journal of Orthopaedic Research* 2005, 23, 802-809), silver ions (Babu et al., *Biomaterials* 2006, 27, 4304-4314; et al., *ACS Applied Materials & Interfaces* 2009, 1, 1553-1560; Hardes et al, *Biomaterials* 2007, 28, 2869-2875), quaternary ammonium salts (Harney et al., *ACS Applied Materials & Interfaces* 2009, 1, 39-41; Pant et al., *Journal of Applied Polymer Science* 2009, 113, 2397-2403; Pant et al., *Journal of Applied Polymer Science* 2007, 104, 2954-2964), and antimicrobial peptides (AMPs) (Hilpert et al., *Chemistry & Biology* 2009, 16, 58-69; Statz et al., *Biofouling* 2008, 24, 439-448). Antimicrobial peptides (AMPs) are a class of short polypeptides usually associated with the host organisms innate immune system (Koczulla et al., *Drugs* 2003, 63, 389-406). AMPs have been identified in a wide range of host organisms, including plants, amphibians, fish and humans (Garcia-Olmedo et al., *Biopolymers* 1998, 47, 479-91; Mangoni et al., *J Pept Sci* 2007, 13, 603-13; Iijima et al., *Eur J Biochem* 2003, 270, 675-86; Pazgier et al., *Cell Mol Life Sci* 2006, 63, 1294-313). AMPs usually consist of 30-100 amino acids and are most often cationic. In addition to a net positive charge, AMPs are often α-helical and amphipathic, containing both hydrophobic and hydrophilic domains. These properties allow for increased interaction with and insertion into negatively charged cell walls and membranes of microbes (Oren et al., *Biopolymers* 1998, 47, 451-63). Additionally, the amphipathic nature of AMPs makes them an excellent candidate for incorporation into self-decontaminating surfaces comprised of a hydrophilic resin. Amphipathic molecules have been shown to surface segregate within such coatings (Harney et al., *ACS Applied Materials & Interfaces* 2009, 1, 39-41), allowing for increased bioavailability of the antimicrobial component.

Due to the prevalence of antibiotic resistance among common human pathogens, recent research into AMPs has revolved around the attempt to increase the availability of drugs to which microbes are susceptible. Because the mechanism of kill for AMPs is different from that of most conventional antibiotics, which tend to be very specific in their targets, AMPs are thought to be a very attractive future substitute for traditional antibiotics. However, in addition to their antimicrobial properties, many of the currently known AMPs exhibit toxicity to human cells as well (Koczulla et al., *Drugs* 2003, 63, 389-406). One possible strategy for reducing the human toxicity of AMPs is the incorporation of amino acid isomers. Nearly all amino acids found in proteins are the L-isomer. The mirror image D-isomers are almost exclusively found in the cell walls of bacteria. However, recent studies suggest that incorporation of D-isomers alongside h-isomers in previously toxic AMPs reduce their toxicity without greatly reducing their antimicrobial activity (Pouny et al., *Biochemistry* 1992, 31, 9482-90).

Several applications for AMPs have been investigated, including therapeutic antibiotics (Koczulla et al., *Drugs* 2003, 63, 389-406; Rossi et al., *Journal of Pharmaceutical Sciences* 2008, 97, 1060-1070), medical devices (Hilpert et al., *Chemistry & Biology* 2009, 16, 58-69; Statz et al., *Biofouling* 2008, 24, 439-448; Cole et al., *Invest Ophthalmol Vis Sci* 2009; McCluskey et al., *ACS Appl Mater Interfaces* 2009, 1, 882-887), and preservatives (Bou-Chacra et al., *Pharmazie* 2007, 62, 199-204; Meyer et al., *J Pharm Sci* 2007, 96, 3155-67). Studies regarding the use of AMPs as active ingredients in the form of surface tethered peptides (Hilpert et al., *Chemistry & Biology* 2009, 16, 58-69; Boulmedais et al., *Biomaterials* 2004, 25, 2003-11; Humblot et al., *Biomaterials* 2009, 30, 3503-12), as well as their use as preservatives in latex coatings as an in-can preservative (Rhoades et al., *Abstracts of Papers of the American Chemical Society* 2005, 230, U4039-U4040; Wicks et al., *Combinatorial Methods and Informatics in Materials Science* 2006, 894, 139-146 356) have been reported. However, no investigations of the addition of AMPs to a coating system as a bulk additive and subsequent post-cure screening for retention of antimicrobial activity have been reported.

Of particular interest to this study are two AMPs recently isolated from the gills of h red sea bream, *Chrysophrys major*. These AMPs, Chrysophsin-1 and -3 (Chr-1 and -3) have demonstrated antimicrobial activity in the low micromolar concentrations against both Gram-positive and Gram-negative bacteria (Iijima et al., T. *Eur J Biochem* 2003, 270, 675-86). However, these compounds have also shown toxicity to human cells, although this toxicity can be reduced by removal of a carboxy-terminal Arg-Arg-Arg-His amino acid sequence not found in other AMPs (Mason et al. *Biochemistry* 2007, 46, 15175-87). The effect that removal of this motif will have on anti-microbial activity has not been investigated.

The mechanisms by which AMPs exert their antimicrobial activity likely vary from peptide to peptide and are thought to be determined by such factors as structure, charge and lipid composition of the target organism (Shai et al., *Peptides* 2001, 22, 1629-41; Shai, *Biochim Biophys Acta* 1999, 1462, 55-70). AMPs with similar structure and charge characteristics to those found in Chr-1 and Chr-3 are thought to act on bacterial membranes via the "carpet" mechanism, wherein cationic peptides coat the cell membrane via electrostatic interactions with the negatively charged phospholipid head groups present in the membrane. This leads to the formation of transient membrane pores, and eventually membrane disintegration (Pouny et al., *Biochemistry* 1992, 31, 12416-23).

BRIEF SUMMARY

Disclosed herein is a composition comprising: a polymeric material and an antimicrobial peptide derived from *Chrysophrys major*.

Also disclosed herein is a method comprising: combining the above polymeric material and antimicrobial peptide to form a coating material; and applying the coating material to a surface.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
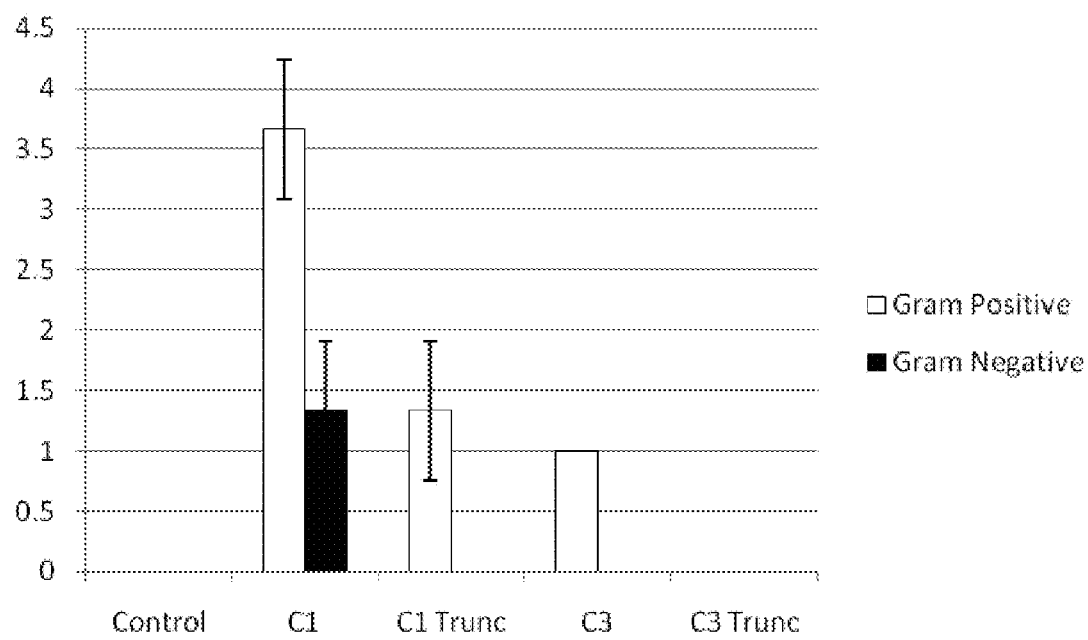
FIG. 1 shows log kill of peptides in a commercial acrylic coating

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is the development of a novel self-decontaminating surface containing AMPs added as a bulk additive into a commercial acrylate coating system. These coatings demonstrate the ability to kill both Gram-positive and Gram-negative bacteria that come into contact with the surface. In addition, the removal of the carboxy-terminal Arg-Arg-Arg-His motif either greatly reduced (Chr-1) or completely abrogated (Chr-3) the antimicrobial activity of the peptides both in solution and in a coating.

Any polymeric material that is compatible with the AMP may be used, including polymeric materials that may be used as a coating on a surface. Such polymeric materials are known in the art. Suitable materials include, but are not limited to, polyacrylics, polyurethanes, epoxies, polyethers, and polymers made from a latex material.

AMPs derived from *Chrysophrys major* are known in the art and include, but are not limited to, Chr-1 and Chr-3 described below. AMPs that are derived from *Chrysophrys major* include modified versions of the AMPs that still retain a degree of antimicrobial activity. Such modifications may include, but are not limited to, truncations, insertions, deletions, and substitutions. The modified AMP may be at least 70%, 80%, 90%, or 95% identical to the natural AMP.

The polymeric material and the AMP may be combined in any known manner, including but not limited to, blending them together. Any method known in the art of applying, the coating material to a surface may be used, including but not limited to, brushing, spraying, and casting.

The ability to produce a self-decontaminating surface consisting of an acrylic resin system and AMPs which self-orient and surface segregate as the resin cures has been demonstrated. While the minimum inhibitory concentration (MIC) results reported here and previously (Iijima et al., *Eur J Biochem* 2003, 270, 675-86) indicate that these peptides are equally effective against Gram-positive and Gram-negative bacteria, this equality was lost when the peptides were incorporated into the coating, perhaps an indication that residues involved in Gram-negative toxicity have become buried within the resin itself. A loose correlation between the MIC data and surface activity was observed, with the most efficacious of the tested peptide containing coatings (Chr-1) able to reduce Gram-positive and Grain-negative bacteria, by 99.9% and 90% respectively after two hours. In addition, removal of the C-terminal RRRH amino acid motif from the peptides either greatly reduced (Chr-1 Truncated) or completely destroyed (Chr-3 Truncated) the antimicrobial activity of the peptides. This strategy is effective in reducing the toxicity of these peptides towards eukaryotic cells (Mason et al., *Biochemistry* 2007, 46, 15175-87).

A direct correlation between an increase in surface contact angle, indicating an increase in hydrophobic moieties, and antimicrobial activity has been demonstrated. While an increase in hydrophobicity at the coating surface does indicate less contact between the coating and bacteria, many previous studies have indicated that the hydrophobic residues present in AMPs are integral to their antimicrobial activity (Oren et al., *Biopolymers* 1998, 47, 451-63; Shai et al., *Peptides* 2001, 22, 1629-41; Shai, *Biochim Biophys Acta* 1999, 1462, 55-70; Pouny et al., *Biochemistry* 1992, 31, 12416-23). Thus, in the case of these coatings, less contact equates to more kill due to the mode of action of the antimicrobial additive. Experiments to determine surface concentration of AMPs utilized a method derived from a commonly used method for quantification of proteins and peptides by bromophenol blue staining (Bonate, *Anal Biochem* 1988, 175, 300-4; Schosinsky et al., *Clin Chem* 1987, 33, 223-6). By utilizing this method to quantify the amount of bromophenol blue bound the surface of our coatings, it was demonstrated that amphipathic AMPs possess the ability to surface segregate, and results showed a direct correlation between surface concentration and antimicrobial activity. The coating with the highest activity, Chr-1, showed a nine-fold increase of surface peptide when compared to the least effective coating. Chr-1 was able to reduce bacterial loads by at least 90% while having only 4.5% of available peptides at the surface.

The following examples are given to illustrate specific applications. These specific examples are not intended to limit the scope of the disclosure in this application.

EXAMPLES

Bacteria and media: Bacterial strains were obtained from the American Type Culture Collection (ATCC, Manassas, Va.) *Staphylococcus aureus* (ATCC 25923) and *Escherichia coli* (ATCC 11229) were used for bacterial Gram-positive and Gram-negative challenges, respectively. Luria-Bertani (LB) media (Difco Laboratories, Detroit, Mich.), prepared as per the manufacturer's specifications, was used as a bacterial growth and dilution medium for preparation of bacteria for Gram-positive and Gram-negative challenges.

Peptides: Peptides Chr-1, Chr-3, Chr-1 Truncated, and Chr-3 Truncated were obtained from Biosynthesis, Inc. (Lewisville, Tex.). Peptides were synthesized then purified by HPLC, Peptides arrived lyophilized, and were resuspended in sterile $H_2O$. For minimum inhibitory concentration (MIC) testing, this suspension was added to media as described below. For surface challenges, this peptide mixture was added to a commercial acrylate coating resin system at 1% (w/w) solids based on the solids of the polymer.

Antimicrobial peptides have been shown to be effective against a broad spectrum of bacteria, viruses and fungi (Hancock et al., *Trends Microbiol* 2000, 8, 402-10; Hancock et al., *Proc Natl Acad Sci USA* 2000, 97, 8856-61). However, many of these peptides, including Chr-1 and Chr-3, also exhibit varying levels of toxicity to eukaryotic cells (Iijima et al., *Eur*

J Biochem 2003, 270, 675-86; Kondejewski et al., J Biol Chem 1999, 274, 13181-92). Chr-1 and -3 contain a Carboxy-terminal Arg-Arg-Arg-His (RRRH) motif not commonly seen in anti-microbial peptides that when removed greatly reduces the hemolytic activity of the peptides. To determine the effect that the removal of this motif on antimicrobial activity both full length peptides as well as truncated peptides lacking the RRRH motifs were studied (Table 1).

TABLE 1

Peptide sequences.

| Peptide | Sequence[a] |
|---|---|
| Chr-1 | FFWLI*K*GAI*H*AG*K*AI*H*GLI*HRRRH* (SEQ. ID. NO. 1) |
| Chr-1 Truncated | FFWLI*K*GAI*H*AG*K*AI*H*GLI*H* (SEQ. ID. NO. 2) |
| Chr-3 | FIGLLISAG*K*AI*H*DLI*RRRH* (SEQ. ID. NO. 3) |
| Chr-3 Truncated | FIGLLISAG*K*AI*H*DLI (SEQ. ID. NO. 4) |

[a]cationic amino acid residues in bold italics

Coating preparation: Films were prepared by combining 25 mg of the respective peptide with 4.95 g acrylate resin (Minwax® Polycrylic®, a water borne polyacrylate resin, 50% w/w solids) with agitation. The final solution was allowed to stir for an additional 30 min and films were cast by brush onto a pre-cleaned aluminum foil. The coatings were allowed to cure at ambient conditions for 24 hours prior to microbial testing. Average thickness of films was determined by a QuaNix 4500 (Automation) paint thickness gauge.

Bacterial challenge: MIC testing: To determine the minimum inhibitory concentration (MIC) of peptides, compounds were weighed and dissolved in sterile water. Each compound was then added to Luria-Bertani (LB) media at concentrations ranging from 0.5 to 0.000667 mg/mL. Bacteria were grown at 37° C. Log phase cells were harvested by centrifugation, counted on a hemocytometer using bright field microscopy, pelleted by centrifugation at 4000×g for 10 min, and resuspended in a 0.5% NaCl solution at a concentration of $1\times10^7$ cfu/mL. To the mixture of LB and biocide was added a 10 pt aliquot containing $1\times10^5$ colony forming units (CFUs) of either *Staphylococcus aureus* (ATCC 25923) for Gram-positive or *Escherichia coli* (ATCC 11105) for Gram-negative. Cultures were then incubated for 18 hr 37° C. with agitation and examined for turbidity. MIC was determined to be the lowest concentration of biocide that prevented visible bacterial growth at 18 hr.

Minimum inhibitory concentrations for peptides in solution were determined and are summarized in Table 2. MIC for the full length peptides have been reported previously (Iijima, et al., T. *Eur J Biochem* 2003, 270, 675-86), and results here are similar. Many antimicrobial compounds thought to act on the exterior structures of organisms (cell wall and/or cell membrane) show varying effective concentrations with compounds frequently showing greater effectiveness against Gram-positive strains than Gram-negative (Cazacu et al., *Journal of Polymer Science Port a—Polymer Chemistry* 2004, 42, 3720-3728; Hazzizalaskar et al., *Journal of Applied Polymer Science* 1995, 58, 77-84; Pant et al., *Journal of Applied Polymer Science* 2008, 110, 3080-3086). However, full length peptides show similar results for both Gram-positive and Gram-negative challenges, Removal of the RRRH motif reduced antimicrobial activity for both Chr-1 Truncated and Chr-3 Truncated, with Chr-3 Truncated showing no measurable antimicrobial activity.

TABLE 2

MIC results for peptides in solution, mg of peptide per mL of culture media

| Peptide | Gram + | Gram − |
|---|---|---|
| Chr-1 | 0.00667 | 0.000667 |
| Chr-1 Truncated | 0.0133 | >0.5 |
| Chr-3 | 0.00667 | 0.0667 |
| Chr-3 Truncated | >0.5 | >0.5 |

Surface testing: Bacteria were grown at 37° C. Log phase cells were harvested by centrifugation, counted on a hemocytometer using bright field microscopy, pelleted by centrifugation at 4000×g for 10 min, and resuspended in a 0.5% NaCl solution at a concentration of $1\times10^7$ cfu/mL. To prevent desiccation of the bacteria during testing, a hydration chamber was prepared. The chamber consisted of a sterile 3×3 in gauze pad placed in the bottom of a sterile 150×15 mm Petri dish. The gauze pad was saturated with 5 mL of sterile water and the test samples placed on top. A 10 µL aliquot containing, $1\times10^5$ bacteria was added to each test coating (280 mm$^2$), and then placed in a hydration chamber at room temperature. After 2 hr of incubation, the remaining bacteria were recovered by placing the coating in a tube containing 5 mL sterile LB media, followed by 30 sec of vortexing. Serial dilutions were carried out, and incubated for 18 hr at 37° C. with agitation. Following incubation, the cultures were examined for the presence of turbidity, indicating bacterial growth. Each coating was tested in triplicate. Log kill was determined by the following: Log kill=5−highest dilution exhibiting bacterial growth. All bacterial challenge procedures were conducted using standard aseptic techniques in a BSL-2 hood.

The coatings contained 1% (w/w) of each peptide in the commercial acrylic resin system. Tested coatings had an average thickness of 0.01 mm as measured by a QuaNix 4500 paint thickness gauge. Similar to the MIC results, Chr-1 showed high activity against both Gram-positive and Gram-negative bacteria, Chr-1 truncated and Chr-3 showed moderate activity, while Chr-3 Truncated showed none (FIG. 1, data in Table 3). As with the MIC testing, removal of the C-terminal RRRH motif greatly reduced (Chr-1 Truncated) or completely removed (Chr-3 Truncated) antimicrobial activity against both Gram-positive and Gram-negative. Unfortunately, the similarity in activity of peptides against Gram-positive and Gram-negative bacteria seen in the MIC results is not present when the peptides are incorporated into a coating.

TABLE 3

Surface Testing Data

| | Grain Positive | | | | | Gram Negative | | | | |
|---|---|---|---|---|---|---|---|---|---|---|
| Sample | Sample 1 Log Kill | Sample 2 Log Kill | Sample 3 Log Kill | Average Log Kill | St. Dev. | Sample 1 Log Kill | Sample 2 Log Kill | Sample 3 Log Kill | Average Log Kill | St. Dev. |
| Control | 0 | 0 | 0 | 0 | 0 | 0 | 0 | 0 | 0 | 0 |
| C1 | 4 | 4 | 3 | 3.6667 | 0.577 | 1 | 2 | 1 | 1.3333 | 0.577 |

TABLE 3-continued

Surface Testing Data

| | Gram Positive | | | | | Gram Negative | | | | |
|---|---|---|---|---|---|---|---|---|---|---|
| Sample | Sample 1 Log Kill | Sample 2 Log Kill | Sample 3 Log Kill | Average Log Kill | St. Dev. | Sample 1 Log Kill | Sample 2 Log Kill | Sample 3 Log Kill | Average Log Kill | St. Dev. |
| C1 Trunc | 1 | 2 | 1 | 1.3333 | 0.577 | 0 | 0 | 0 | 0 | 0 |
| C3 | 1 | 1 | 1 | 1 | 0 | 0 | 0 | 0 | 0 | 0 |
| C3 Trunc | 0 | 0 | 0 | 0 | 0 | 0 | 0 | 0 | 0 | 0 |

Surface Energy and Contact Angle: Surface energy and contact angle measurements were performed using a VCA 2500 video contact angle system by AST Products, Inc. Contact angle measurements using the sessile drop technique. An image was captured of the interface 15 sec after application and contact angle was measured.

Due to the complex nature of coating and difficulty in ascertaining the surface segregating ability of the peptide. The surface contact angle method was used and subsequent critical surface energy calculations were based on the data obtained. In all cases the surface became more hydrophobic as indicated by the significant increase in contact angle for water. The data generated from ethylene glycol were not significantly different thus no trend could be drawn, and methylene iodide was consistent with the water data. The critical surface energy was also significantly altered upon addition of all peptides described (Table 4). Upon subsequent analysis, a correlation was observed between critical surface energy and surface antimicrobial properties, especially Gram-positive, and to a much lesser extent Gram-negative. This result is consistent with past reports of surface segregation of amphipathic antimicrobial compounds within hydrophilic resin systems (Harney et al., *ACS Applied Materials & Interfaces* 2009, 1, 39-41).

TABLE 4

Contact angle measurements and critical surface energy.

| Peptide | $H_2O$ | $CH_2OHCH_2OH$ | $CH_2I_2$ | Critical Surface Energy (dynes/cm) |
|---|---|---|---|---|
| Control | 38.27(±3.05) | 60.62(±2.00) | 58.72(±5.30) | 90.67 |
| Chr - 1 | 53.05(±4.04) | 60.77(±3.35) | 69.45(±4.81) | 131.6 |
| Chr - 1 Truncated | 50.00(±2,66) | 65.80(±3.43) | 62.73(±4.20) | 111.9 |
| Chr - 3 | 43.88(±5.01) | 63.02(±3.51) | 64.57(±3.52) | 97.22 |
| Chr - 3 Truncated | 46.90(±2.96) | 62.67(±1.90) | 70.28(±3.80) | 101.7 |

Surface Segregation of Peptide: Each 280 mm² section of the test coating was submerged in 0.5% bromophenol blue for one minute. Coatings were then removed and washed three times with 20 mL di-$H_2O$. Bromophenol blue was then recovered from the test samples using 0.05 M HCl in ethanol. Absorbance at 600 nm was determined using a Cary 5E UV-Vis-NIR (Varian, Walnut Creek, Calif.). Beer's Law was used to determine concentration of bromophenol blue and thus concentration of peptides at the surface of the coatings.

Figure 2:
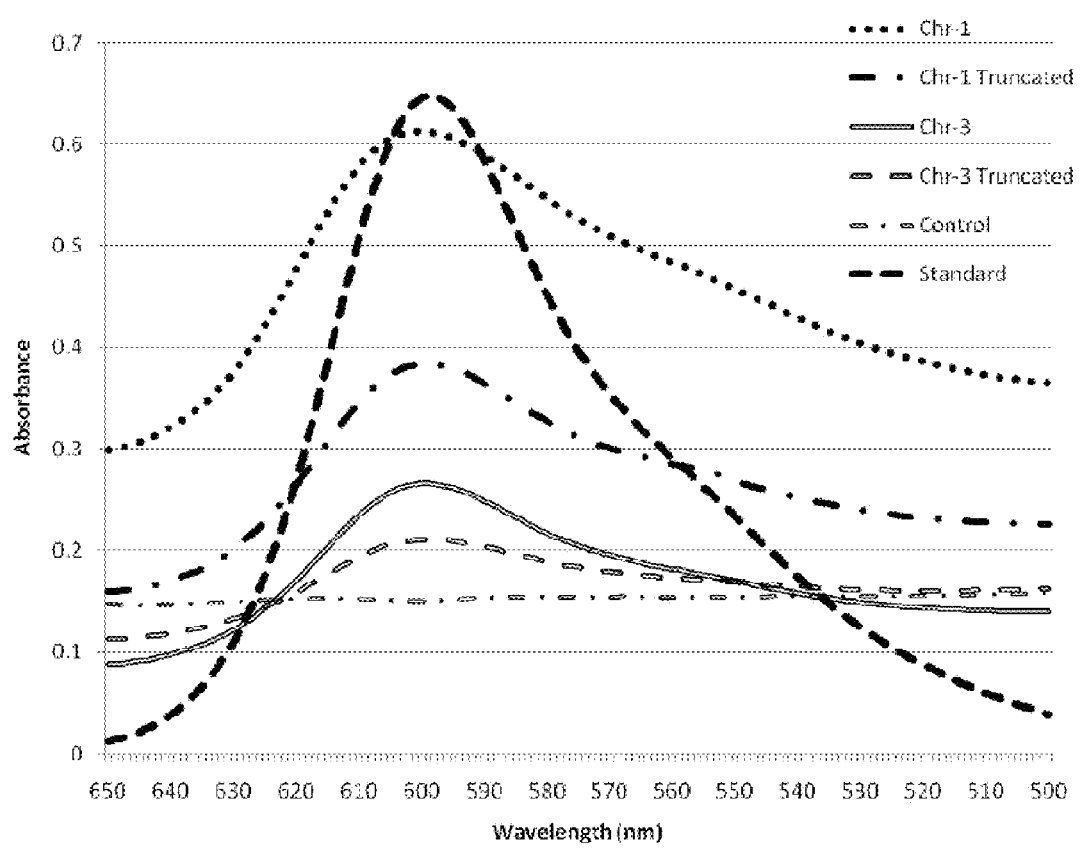
FIG. 2 shows absorbance at 600 nm of bromophenol blue reacted with peptide coatings

Bromophenol blue has been used extensively to quantify the amount of protein or peptide in a solution (Bonate, *Anal Biochem* 1988, 175, 300-4; Schosinsky et al., *Clin Chem* 1987, 33, 223-6). A test method to visualize surface peptide using bromophenol blue was adapted from these solution test methods. To determine the extent which peptides were segregated to the surface of test coatings, each coating was reacted with an aqueous solution containing 0.5% bromophenol blue. This solution provided molar excess of bromophenol blue that was able to undergo an acid-base reaction with the amines of the peptide at a 1:1 ratio. The reaction was then reversed, and the bromophenol blue recovered with 0.05 M in ethanol. The absorbance of this solution at 600 nm was determined and Beer's Law was used to determine the concentration of bromophenol blue (FIG. 2). This could be directly converted into number of peptides at the surface and correlated directly to the effectiveness of each coating. An approximate 9 fold increase in the amount of surface peptide present in the best coating (Chr-1) was demonstrated as compared to the surface peptide present in the least effective coating (Chr-3 Truncated) (Table 5).

TABLE 5

Molecules of peptide at surface of coating, with percentage of total peptide shown in parentheses.

| Sample | Molecules Peptide per mm² (% of total) |
|---|---|
| Chr-1 | $6.8 \times 10^{13}$ (~4.5%) |
| Chr-1 Truncated | $3.5 \times 10^{13}$ (~2%) |
| Chr-3 | $1.9 \times 10^{13}$ (~1%) |
| Chr-3 Truncated | $1.0 \times 10^{13}$ (~0.5%) |

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A composition comprising:
   a polymeric material; and
   an antimicrobial peptide derived from *Chrysophrys major*;
   wherein the antimicrobial peptide is FFWLIKGAIHAGKAIHGLIHRRRH (SEQ. ID. NO. 1) or FFWLIKGAIHAGKAIHGLIH (SEQ. ID. NO. 2).

2. The composition of claim 1, wherein the composition is in the form of a coating.

3. The composition of claim 1, wherein the polymeric material is a polyacrylic, a polyurethane, a polyepoxy, or made from a latex material.

4. A method comprising:
   combining a polymeric material with an antimicrobial peptide derived from *Chrysophrys major* to form a coating material; and
   applying the coating material to a surface;
   wherein the antimicrobial peptide is FFWLIKGAIHAGKAIHGLIHRRRH (SEQ. ID. NO. 1) or FFWLIKGAIHAGKAIHGLIH (SEQ. ID. NO. 2).

5. The method of claim 4, wherein the composition is in the form of a coating.

6. The method of claim 4, wherein the polymeric material is a polyacrylic, a polyurethane, an epoxy, a polyether, or is made from a latex material.

* * * * *

SEQUENCE LISTING

<160> NUMBER OF SEQ ID NOS: 4

<210> SEQ ID NO 1
<211> LENGTH: 24
<212> TYPE: PRT
<213> ORGANISM: Chrysophrys major -continued

```
<400> SEQUENCE: 1

Phe Phe Trp Leu Ile Lys Gly Ala Ile His Ala Gly Lys Ala Ile His
1               5                   10                  15

Gly Leu Ile His Arg Arg Arg His
            20

<210> SEQ ID NO 2
<211> LENGTH: 20
<212> TYPE: PRT
<213> ORGANISM: Chrysophrys major

<400> SEQUENCE: 2

Phe Phe Trp Leu Ile Lys Gly Ala Ile His Ala Gly Lys Ala Ile His
1               5                   10                  15

Gly Leu Ile His
            20

<210> SEQ ID NO 3
<211> LENGTH: 20
<212> TYPE: PRT
<213> ORGANISM: Chrysophrys major

<400> SEQUENCE: 3

Phe Ile Gly Leu Leu Ile Ser Ala Gly Lys Ala Ile His Asp Leu Ile
1               5                   10                  15

Arg Arg Arg His
            20

<210> SEQ ID NO 4
<211> LENGTH: 16
<212> TYPE: PRT
<213> ORGANISM: Chrysophrys major

<400> SEQUENCE: 4

Phe Ile Gly Leu Leu Ile Ser Ala Gly Lys Ala Ile His Asp Leu Ile
1               5                   10                  15
```